(12) United States Patent
Neeley et al.

(10) Patent No.: US 11,583,453 B2
(45) Date of Patent: Feb. 21, 2023

(54) PERSONAL HYGIENE DEVICE FOR DETECTING A FLUID

(71) Applicant: Johnson & Johnson Consumer Inc., Skillman, NJ (US)

(72) Inventors: William Chester Neeley, Melbourne, FL (US); Randall B. Pugh, St. Johns, FL (US); Adam Toner, Jacksonville, FL (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 829 days.

(21) Appl. No.: 16/106,463

(22) Filed: Aug. 21, 2018

(65) Prior Publication Data
US 2020/0060899 A1 Feb. 27, 2020

(51) Int. Cl.
*A61F 13/42* (2006.01)
*A61F 13/84* (2006.01)
*A61F 13/472* (2006.01)
*A61F 13/49* (2006.01)
*G16H 40/40* (2018.01)
*A61B 5/15* (2006.01)
*A61B 5/00* (2006.01)
*A61B 10/00* (2006.01)
*G08B 21/24* (2006.01)

(52) U.S. Cl.
CPC .............. *A61F 13/84* (2013.01); *A61F 13/42* (2013.01); *A61F 13/472* (2013.01); *A61F 13/49* (2013.01); *A61B 5/1405* (2013.01); *A61B 5/150045* (2013.01); *A61B 5/150969* (2013.01); *A61B 5/6808* (2013.01); *A61B 2010/0074* (2013.01); *A61F 2013/421* (2013.01); *A61F 2013/424* (2013.01); *A61F 2013/427* (2013.01); *A61F 2013/8479* (2013.01); *G08B 21/245* (2013.01); *G16H 40/40* (2018.01)

(58) Field of Classification Search
CPC .............. A61F 13/20–208; A61F 13/42; A61F 2013/424; A61F 2013/421–428
See application file for complete search history.

(56) References Cited

U.S. PATENT DOCUMENTS 5,264,830 A * 11/1993 Kline ...................... A61F 13/42
128/886
2004/0064114 A1 4/2004 Benoit et al.
(Continued)

FOREIGN PATENT DOCUMENTS

CN 2121226 U 11/1992
WO WO 2010/123425 A 10/2010

OTHER PUBLICATIONS

International search report dated Dec. 13, 2019, for international application PCT/IB2019/057016.

*Primary Examiner* — Susan S Su

(57) ABSTRACT

A personal hygiene device may have a main body with an absorbent material configured to absorb a fluid, a sensor disposed within the main body, and a controller configured to communicate with the sensor. The sensor has a conductor and an insulator containing at least a portion of the conductor, and the sensor is configured to detect a first electrical value and a second electrical value that is different from the first electrical value. The sensor is also configured to transmit a signal to the controller upon detection of the second electrical value.

11 Claims, 16 Drawing Sheets

(56) References Cited

U.S. PATENT DOCUMENTS

| | | | |
|---|---|---|---|
| 2010/0305530 A1* | 12/2010 | Larkin | A61F 13/2051 |
| | | | 604/361 |
| 2012/0040655 A1* | 2/2012 | Larkin | A61B 5/0002 |
| | | | 455/418 |
| 2013/0131618 A1 | 5/2013 | Kollakompil et al. | |
| 2013/0307570 A1 | 11/2013 | Bosaeus et al. | |
| 2016/0374868 A1 | 12/2016 | Ettrup Hansen | |
| 2017/0035622 A1* | 2/2017 | Wang | A61F 13/42 |

* cited by examiner

PERSONAL HYGIENE DEVICE FOR DETECTING A FLUID

TECHNICAL FIELD

The present disclosure relates generally to a personal hygiene device configured to detect the presence of fluid, and in particular to a personal hygiene device comprising a capacitance sensor.

BACKGROUND

Many types of personal hygiene devices (e.g., products) exist in the market today. Examples of such personal hygiene devices include tampons, bed pads, disposable diapers, and disposable sanitary napkins. In particular, feminine hygiene products may be used during a woman's menstrual cycle. Women may experience various menstrual flows over the course of each cycle, with some days having a heavier menstrual flow than other days. Because of this variance in flow, it is sometimes difficult to accurately predict and judge when a hygiene product should be used or replaced. This often causes personal hygiene products to become oversaturated leading to potential accidents or overflow beyond the absorbent area of the product. Furthermore, continued use of an oversaturated hygiene product may lead to negative health side-effects, such as toxic shock syndrome and other infections.

Many women manually track or monitor their menstrual cycle for predictability to avoid the unexpected start of menstruation in the absence of a personal hygiene product or accidents of the sort discussed above. There are over two hundred smart device applications available to monitor menstruation manually. Users enter data into the application on a smart device, for example a smart phone or other hand-held device, and the application generates data predicting, for example, menstrual start day, flow pattern, and length of menstruation. Many of these smart device applications issue alerts when menstruation is expected to start and end. All available devices, however, rely on data based on the subjective and manual entry of the user and may not reliably meet the primary needs most female hygiene product users have; namely, predictability and reliability. None of these applications are able to actively monitor the active absorption capacity of a personal hygiene product while a user is wearing or using it.

In addition to the need for predictability and reliability in use of a personal hygiene product, a personal hygiene product is situated either proximate to or inserted into the body and as a result is able to collect data about patterns of discharge and biometrics in a way that a manual-entry application is unable to capture. This data is beneficial, to avoid social embarrassment, and also for a user's overall health, for example, to provide accurate data to a physician or to alert the user if there are disruptions in normal patterns of bodily fluid discharge.

For example, menstrual issues and patterns of discharge are one of the most common reasons for a woman to see a doctor. Generally, a doctor's first response will be for the woman to keep a "menstrual diary" as a record of the period dates, length of periods, flow, etc. Menstruation that departs from a normal monthly cycle, such as lasting longer or shorter than usual or not occurring at all, may indicate an underlying health issue. For example, abnormally long menstrual bleeding may indicate irregularities such as polyps, fibroids, cancer or infection within the uterus or cervix. A number of conditions may be revealed from menstrual flow data; including dysmenorrhea (painful periods); oligomenorhoea (irregular periods); amenorrhea (lack of periods); and menorrhagia (heavy periods).

The location of a personal hygiene product may enable it to gather internal and external biometric data such as temperature or pH. Menstruation, for example, also includes discharge with biometric information. Monthly menstruation involves a process in which the uterus sheds the endometrium to allow a new lining to replace it. Menstrual fluid comprises uterine blood, meaning the endometrial tissue, vaginal secretions, and cervical fluids. Menstrual fluid also includes information through hormones such as estrogen and progesterone and enzymes related to pregnancy such as hydrolytic enzymes and lysosomes.

In the home health setting, for example, individuals receive periodic check-ups by home health staff ranging from multiple times daily to weekly. Isolated visits may not capture or accurately give warning if an individual has additional health issues if those issues do not present during a check-up. The valuable biometrics that may be gleamed from a personal hygiene product would accurately convey extensive data that if available electronically to a health professional would provide a more accurate and holistic understanding of the patient's health. Additionally, a personal hygiene product with a sensor system may facilitate remote monitoring either by a health care professional or family member.

The proper combination of a personal hygiene product incorporated with a sensor system capable of interfacing with a smart hand-held electronic device would meet the ultimate needs of personal hygiene product consumers. The sensor system needs to be biocompatible and comprise an array capable of wireless communication. Accordingly, there exists a need for providing a personal hygiene product capable of gathering, processing, and communicating data about the product's absorbent capacity and individual user's bodily fluid discharge to the smart hand-held electronic device of a user. There are also exists a need for an individual user to be able to interface with the data once communicated to the smart hand-held electronic device.

SUMMARY

A personal hygiene device according to the present invention may have a main body with an absorbent material configured to absorb a fluid, a sensor disposed within the main body, and a controller configured to communicate with the sensor. The sensor may be or comprise a conductor and an insulator disposed adjacent at least a portion of the conductor. The sensor may be or comprise a capacitive sensor and/or may comprise a pair of insulated conductors spaced from each other. The sensor may be configured to detect a first electrical value and/or a second electrical value that is different from the first electrical value. Such electrical values may be or comprise electric field strength, permittivity, and/or a capacitance, or other electrical values. The sensor may be configured to transmit a signal to the controller indicative of the detected electrical value.

In some aspects, the conductor may be or comprise a plurality of conductors (e.g., a pair of conductors), for example, at least a pair of linear conductors, each of which are substantially parallel to one another. A capacitive sensor for detecting the presence of a fluid according to the present invention may comprise the plurality of conductors and an insulating material positioned adjacent each conductor in the plurality of conductors. At least a portion of the insulating material is disposed between at least two of the plurality of conductors. The plurality of conductors may be configured to have a first capacitance value when fluid is not present within the sensor and a second capacitance value when fluid is present in the sensor. The sensor may be configured to detect an absolute measurement of an electrical characteristic and/or a relative measurement such as change from a first capacitance to a second capacitance. Such measurements may be analyzed and may be communicated to a user of the personal hygiene device.

BRIEF DESCRIPTION OF THE DRAWINGS

The present application is further understood when read in conjunction with the appended drawings. For the purpose of illustrating the subject matter, there are shown in the drawings exemplary aspects of the subject matter; however, the presently disclosed subject matter is not limited to the specific methods, devices, and systems disclosed. Furthermore, the drawings are not necessarily drawn to scale. In the drawings.

DETAILED DESCRIPTION OF ILLUSTRATIVE ASPECTS

Figure 1:
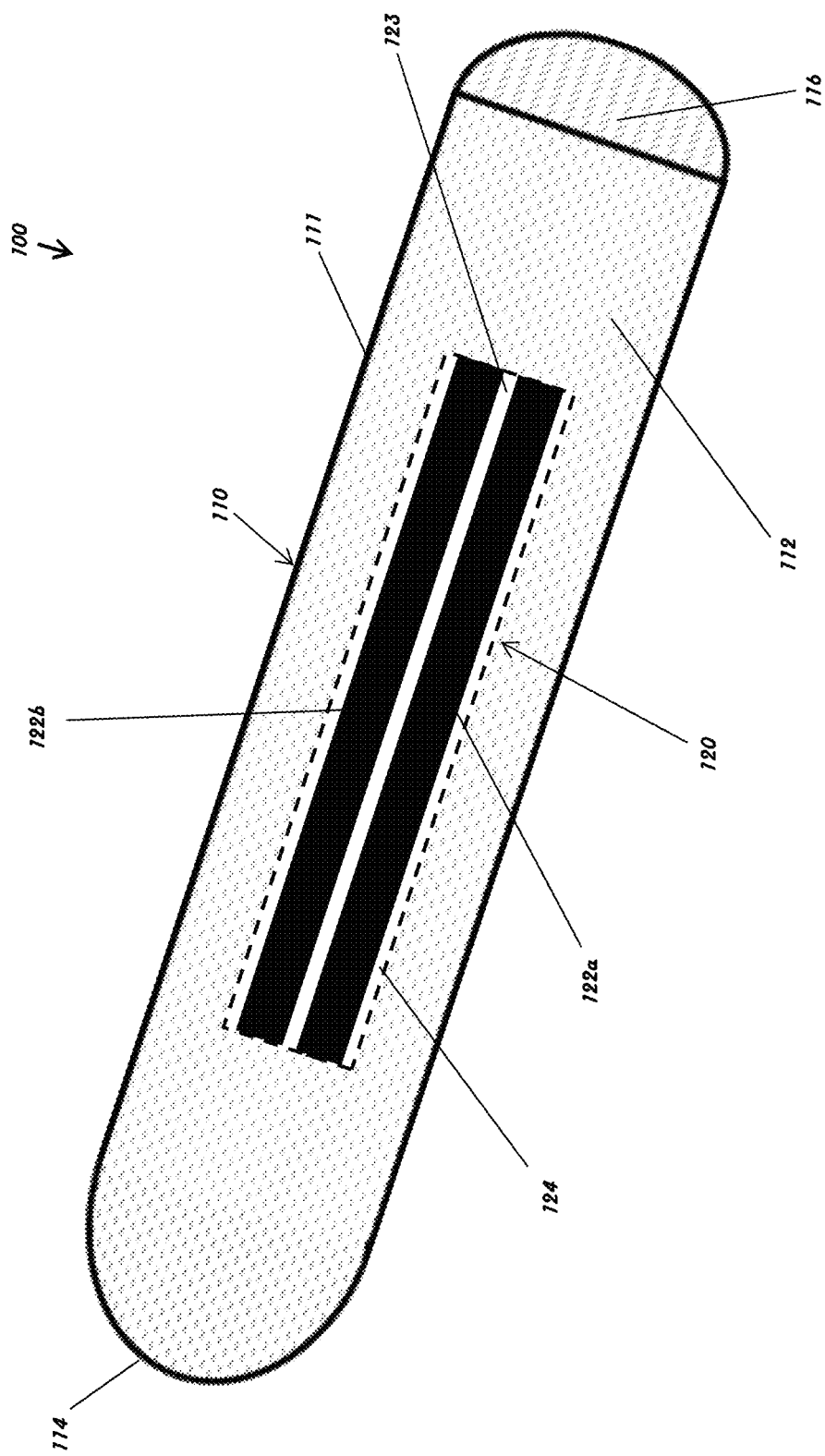
FIG. 1 illustrates a side cross-sectional view of a personal hygiene device according to an aspect of the present disclosure.

Aspects of the disclosure will now be described in detail with reference to the drawings, wherein like reference numbers refer to like elements throughout, unless specified otherwise. Certain terminology is used in the following description for convenience only and is not limiting.

A device (e.g., hygiene product) comprising a sensor system capable of interface with a smart, hand-held, electronic device is disclosed in this application. In the following sections, detailed descriptions of various aspects are described. The descriptions of various aspects are illustrative aspects, and various modifications and alterations may be apparent to those skilled in the art. Therefore, the exemplary aspects do not limit the scope of this application. The sensor system is designed for use in or adjacent to the body of a living organism.

The device may be optimized to accurately detect a signal. A sensor of the device may be optimized to maximize a change in capacitance on exposure to a fluid. This optimization may be done by altering the cross section of one or more conductors of the sensor so the electric field between the one or more conductors encounters less of the insulator (fixed) and more of the fluid (variable). For example, the cross section may be formed with an elliptical shape. To fully maximize the change in capacitance, the one or more conductors may be surrounded by very thin and/or sharp insulation, such as a flat ribbon cable. This shape is not desired due to comfort concerns. An optimized cross section may be based on a balance between capacitance, comfort, cost, and/or the like. An optimized cross section may be implemented by using an elliptical extrusion die when producing insulated ribbon cable. Treatment, for example head and rolling, may be applied to classical ribbon cable having circular cross sections.

The device may be optimized by using a separator between the one or more conductors of the sensor. A portion of the separator may be implemented with a hydrogel or similar fluid-permeable material. The separator may be configured to provide a controlled separation between the one or more conductors. The separator may be configured to prevent shorting. The separator may be configured to establish a baseline capacitance (e.g., a dry capacitance). The insulator (e.g., which may be impermeable to fluids) may be at least partially removed (e.g., exposing the conductors) between the conductors. The portion of the insulator that is removed may be replaced with a permeable material such as a hydrogel. In some scenarios the insulator may be formed with a gap or with a portion comprising permeable material. At least a portion of the remaining insulator may provide an electrical open. The insulator and hydrogel may both act to mechanically separate the conductors. As the sensor is exposed to fluid, fluid can now permeate directly between the conductors. This configuration may have an increased change in capacitance on exposure to fluid (e.g., resulting in improved accuracy). The sensor may be formed using a co-extrusion process.

The device may further be optimized by applying a surface-treatment to the insulator and/or separator. The surface treatment may increase uptake of fluid (e.g., resulting in a faster and more accurate sensing for the user). The surface treatment may also be applied to a tampon comprising the device. The fibrous filler in a tampon, especially under heavy compression, may fill the space outside the sensor insulation and act to carry fluid close to the conductors. Surface treatment of the fibers and/or sensor insulation may improve sensor speed and accuracy. This treatment may be especially important if a particular insulator is optimized for cost, abrasion resistance, dielectric constant, etc. which could be at odds with surface energy.

In certain aspects, the sensor system of the present disclosure may be or comprise a capacitance sensor. An exemplary capacitance sensor may comprise at least a pair of linear conductive leads spaced from each other and configured to generate an electric field between each other when electric potential is applied across the conductive leads. The conductive leads may comprise one or more of a conductive wire, a conductive thread, or a conductive yarn. The conductive yarn may comprise a yarn that has been treated (e.g., covered) with a conductive material. The conductive thread may comprise a thread that has been treated (e.g., covered with a conductive material).

The capacitance sensor may comprise an insulator. The insulator may be one or more of hydrophilic, hydrophobic, omniphilic, omnophobic, oleophilic, or oleophobic. For example, the insulator may be treated to cause a surface of the insulator to be one or more of hydrophilic, hydrophobic, omniphilic, omnophobic, oleophilic, or oleophobic. The insulator may be disposed between an absorbent material and at least a portion of each of the conductive leads. As an example, an electrically insulative material may be disposed about at least a portion of each of the linear conductive leads. As such, the insulative material may be disposed between each of the linear conductive leads. The insulative material may also insulate the linear conductive leads from the absorbent material. Accordingly, when electrical current is applied to one or more of the linear conductive leads, an electric field is generated between the linear conductive leads. The linear conductive leads and the electrical current are configured such that at least a portion of the generated electric field passes through the absorbent material. As a fluid level (e.g., saturation) of the portion of the absorbent material in the generated electric field changes, electrical characteristics (e.g., capacitance) of the dielectric or other materials in the field may change. Such a change may be measured and may be indicative of the fluid level of the personal hygiene device incorporating the sensor system. As an example, the sensor system may be configured to detect a first capacitance value and a second capacitance value that is different from the first capacitance value.

A controller may be integrated with or configured to communicate with the sensor system (e.g., capacitance sensor). As measurement of electrical characteristics of the capacitance sensor is made, a signal may be transmitted to the controller. The signal may be indicative of one or more of a first capacitance value and a second capacitance value. As described herein, the first capacitance value and the second capacitance value may be dependent upon the presence of a fluid within the electric field between the linear conductive leads when electric current is applied to one or more of the linear conductive leads. The controller may be configured to analyze the received signal and may determine an associated fluid level (e.g., saturation). Such determination may be an absolute or relative determination. Moreover, the controller may communicate the associated fluid level to a user of the device, for example, via a user interface.

Figure 2:
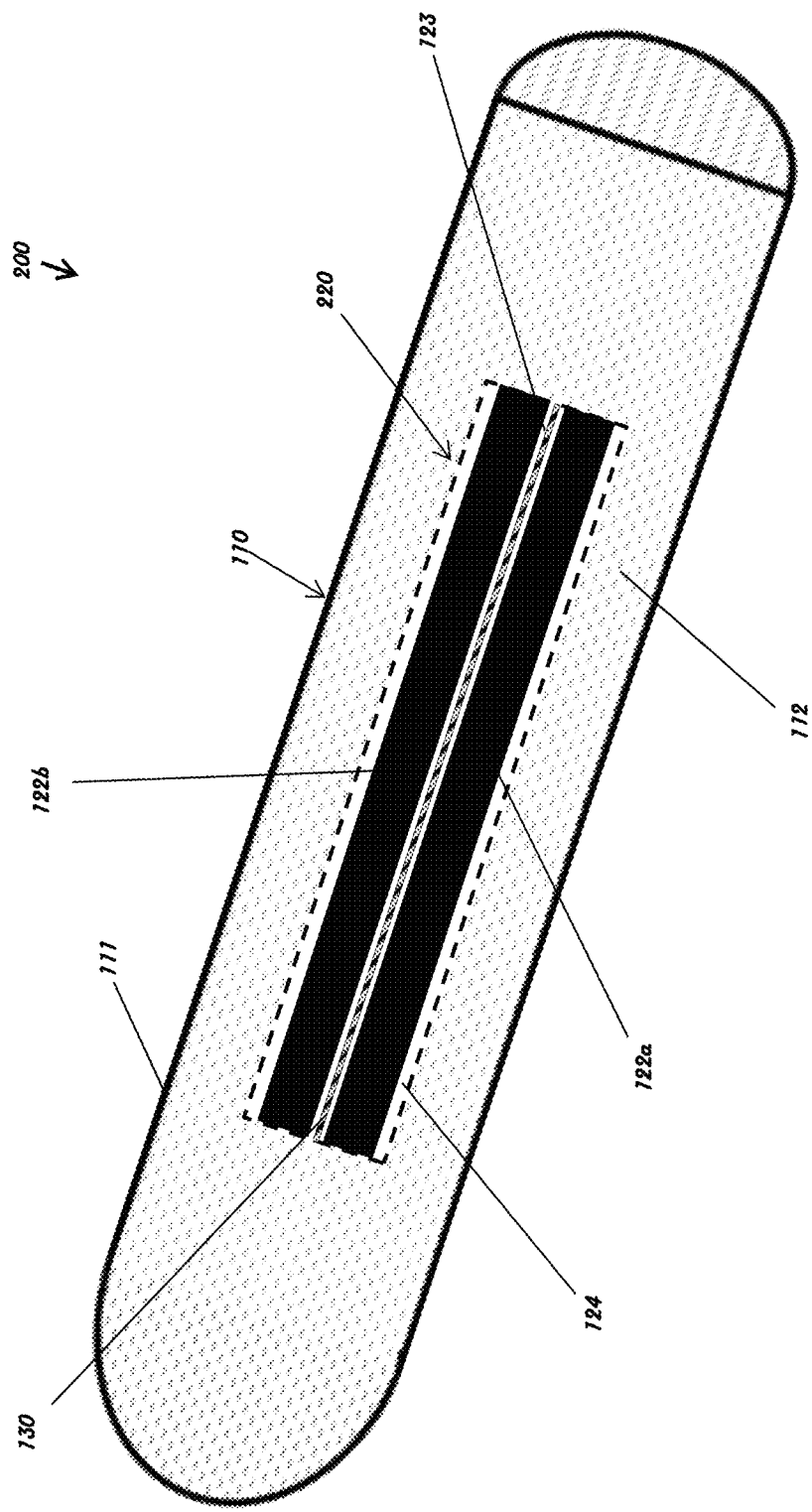
FIG. 2 illustrates a top cross-sectional view of the aspect illustrated in FIG. 1.

Referring to FIGS. 1 and 2, a personal hygiene device 100 comprises a main body 110 (e.g., substrate, housing, etc.) with a sensor 120, 220 disposed adjacent, embedded within, or attached thereto. The personal hygiene device 100 may be or comprise a tampon configured for insertion into the body. The personal hygiene device 100 may also comprise a bed pad, diaper, sanitary napkin, undergarment liner, surgical dressing, or another personal hygiene item configured to absorb liquid.

The main body 110 may be formed from or may comprise an absorbent material 112. The absorbent material 112 may be configured to absorb liquid that comes in contact with the material, for example, bodily fluids, and specifically menstrual fluids. The main body 110 may comprise one absorbent material 112, or it may include a combination of materials. The absorbent material 112 may have an inner core and an outer core (not shown) that include different compositions of material. In some aspects, the absorbent material 112 may include cotton, rayon, polyester, polypropylene, polyethylene, or another suitable absorbent material. The personal hygiene device of some aspects may be designed to directly contact with, or insert into, the human body, and the absorbent material of such aspects should be biocompatible with the human body so as to avoid an adverse reaction upon contact with or insertion therein.

With further reference to FIGS. 1 and 2, the main body 110 has a proximal end 114 and a distal end 116. In some aspects, the main body 110 may be substantially cylindrical, extending from the proximal end 114 to the distal end 116. It will be appreciated by those skilled in the art that the exact measurements of a personal hygiene device may vary depending on application and individual needs of users. In some non-limiting aspects, the main body 110 may be less than three inches in length. However, other implementations and sizes may be used. In some aspects, the absorbent material 112 within main body 110 may be configured to absorb liquid and expand accordingly. Once again, those skilled in the art will appreciate that the absorbance capacity may vary amongst aspects depending on application and individual needs of the user, for example, the duration and volume of a user's menstrual cycle. Some aspects absorb lower amounts of liquid, for example less than six grams. Other aspects may be configured to absorb higher quantities of liquid, such as up to six grams, up to nine grams, up to twelve grams, up to fifteen grams, or up to eighteen grams of liquid. It will be understood that some aspects may be configured to absorb greater than eighteen grams of liquid, and the above volumes should not be construed as limiting the disclosure.

The personal hygiene device 100 may comprise a sensor system such as sensor 120. The sensor 120, 220 may be fixedly secured to the main body 110, or it may be removably attached to the main body 110. In some aspects, the sensor 120, 220 may be embedded within the absorbent material 112. Alternatively, the sensor 120, 220 may be positioned at or proximal to the exterior surface 111 of the main body 110. Referring to FIGS. 1 and 2, the sensor 120, 220 is fully encapsulated within the absorbent material 112. In some aspects, the sensor 120, 220 may be partially encapsulated within the absorbent material 112. The sensor 120, 220 may extend substantially the length of the main body 110, or it may be shorter than the main body 110.

Figure 14:
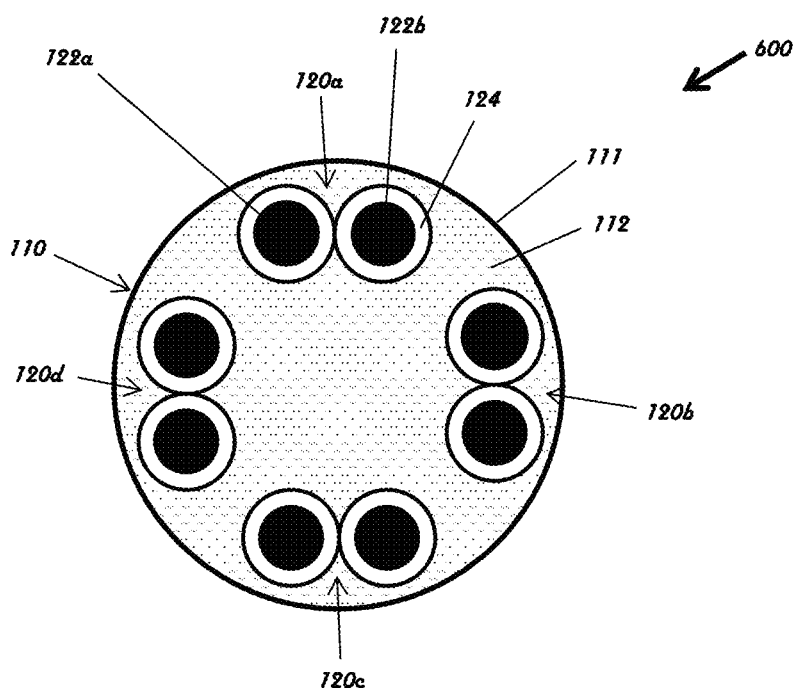
FIG. 14 illustrates a top cross-sectional view of a personal hygiene device according to yet another aspect of the present disclosure.
Figure 17:
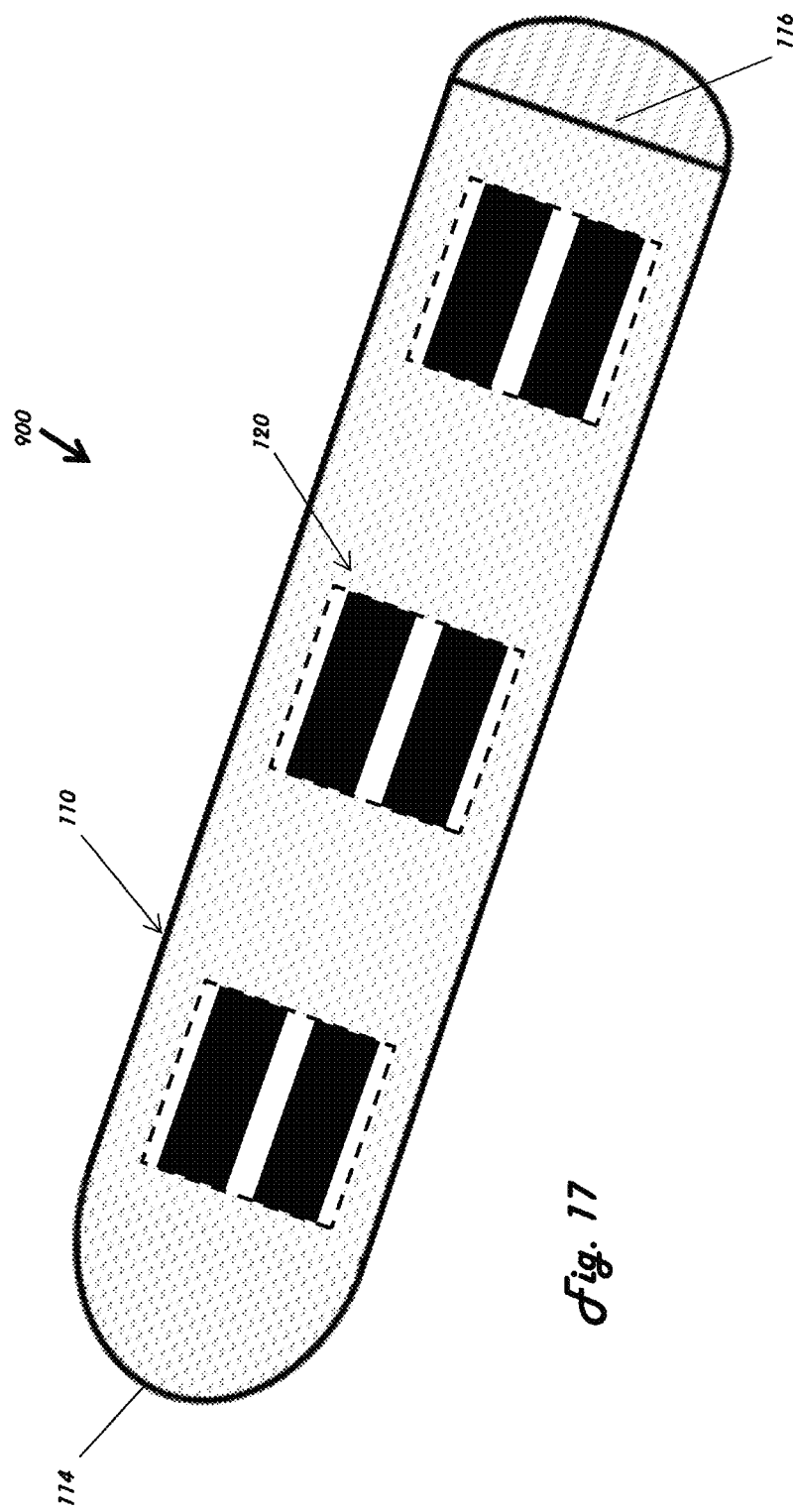
FIG. 17 illustrates a side cross-sectional view of a personal hygiene device according to yet another aspect of the present disclosure.

The sensor 120, 220 may be positioned approximately in the center of the main body 110 when viewed along an axial direction extending from the proximal end 114 to the distal end 116. In some aspects, the sensor 120, 220 may be closer to the exterior surface 111 of the main body 110 than to the center as shown in the illustrative aspect of FIG. 14. In some aspects, the personal hygiene device 100 may include a plurality of sensors 120 (FIG. 2 sensor 220). According to FIG. 14, each of the sensors 120 (FIG. 2 sensor 220) may be positioned radially around the center of the main body 110. Referring to FIG. 17, multiple sensors 120 (FIG. 2 sensor 220) may be positioned throughout the main body 110 such that at least some of the sensors 120 are disposed at different distances from the proximal end 114. In some aspects, the personal hygiene device 100 may include two, three, four, five, six, seven, or eight sensors 120 (FIG. 2 sensor 220). The quantity of sensors is not limiting, and a personal hygiene device 100 may include a different suitable quantity of sensors. The sensors 120, 220 may have the same dimensions and parameters, or they may be different. In some aspects, the plurality of sensors 120, 220 may include sensors of different sensing types. For example, some personal hygiene devices may include a sensor that detects moisture, a sensor that detects consistency of a liquid (e.g., the type of liquid), the amount of absorbed liquid, a physical change in size of the device (e.g., expansion of the absorbent material 112 after absorption of liquid), or another sensing parameter that may be advantageous to include in an aspect of a personal hygiene device.

In another aspect, the sensor 120, 220 may be a capacitive sensor and include a capacitor. The sensor may include a conductor that contacts an insulating material 124. In some aspects, sensor 120, 220 includes a plurality of conductors. Referring to FIGS. 1 and 2, the sensor 120, 220 may have a first conductor 122*a* and a second conductor 122*b*, each conductor having a length and extending approximately parallel to the other conductor. The first conductor 122*a* and the second conductor 122*b* may be configured to have a voltage or potential difference therebetween. As such, the sensor 120, 220 may be a capacitive sensor in that the first conductor 122*a* and the second conductor 122*b* operate as a capacitor. As such, the sensor 120, 220 (comprising the first conductor 122*a* and the second conductor 122*b*) may be configured to detect the capacitance, change in the capacitance, and/or change in potential difference based on the detected environment of the first conductor 122*a* and the second conductor 122*b*.

The sensor 120, 220 may include insulating material 124 configured to insulate at least a portion of the conductor from the absorbent material 112 of the personal hygiene device 100. It will be understood by a person skilled in the art that an insulating material may include many different materials having varying conductive properties. The insulating material 124 may include plastics, rubbers, fluoropolymers, naturally-occurring materials, or another suitable material having insulating properties. The insulating material 124 may include or may be formed from thermoplastic urethane (TPU). Additionally, or alternatively, suitable materials may include, but are not limited to, polyvinyl chloride, polyethylene, polypropylene, polyurethane, thermoplastic rubber, neoprene, styrene butadiene rubber, silicone, fiberglass, ethylene propylene rubber, ethylene propylene diene monomer, polytetrafluoroethylene, thermoplastic elastomer, or a combination of the preceding.

Insulating material 124 may have various thicknesses. In some illustrative aspects, for example, the thickness may be less than about 1 mm. In further aspects, the thickness may be less than 0.3 mm, or may be between 0.1 mm and 1 mm in thickness.

In some aspects, the insulating material 124 may also include a coating (not shown) on its surface. The coating may include various materials that improve sensor resilience, speed, and/or accuracy. A non-limiting example of a suitable coating includes thermoplastic polyurethane (TPU). Other coatings may be used to configure wettability and other physical and electrical characteristics. As a further example, the insulating material 124 may be formed from the TPU with a loading of up to 100 percent by weight of the total weight of the insulating material 124.

Figure 3:
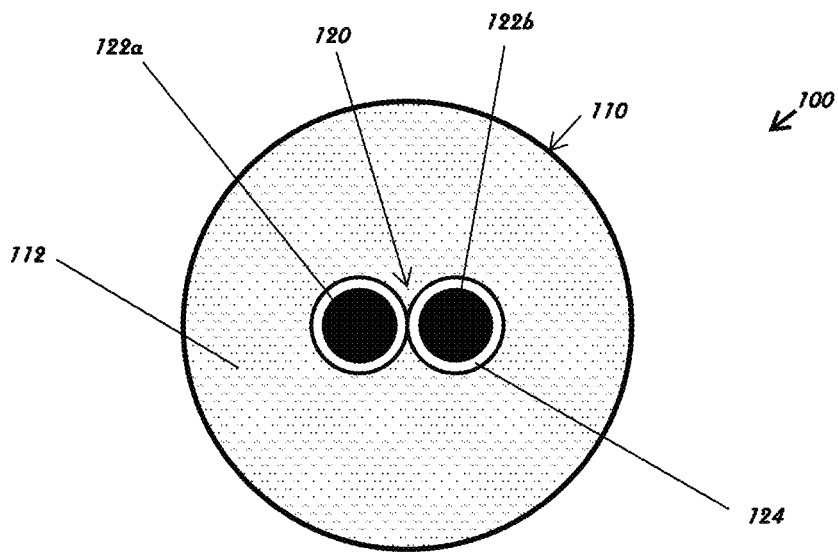
FIG. 3 illustrates a side cross-sectional view of a personal hygiene device according to another aspect of the present disclosure.
Figure 4:
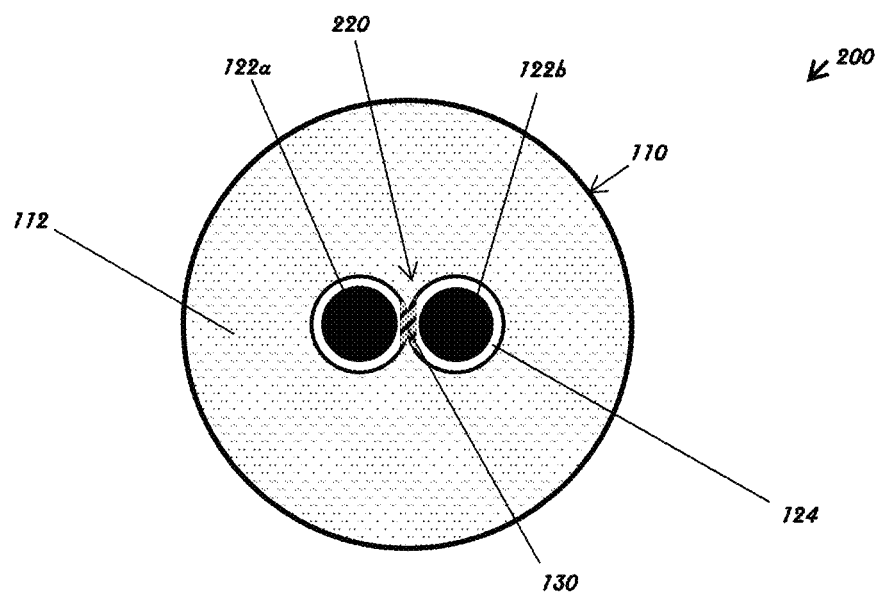
FIG. 4 illustrates a top cross-sectional view of the aspect illustrated in FIG. 3.
Figure 5:
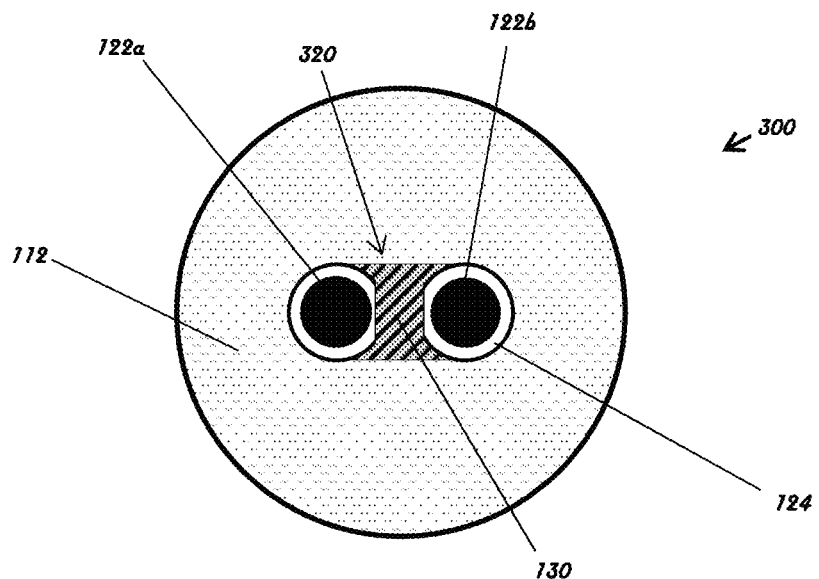
FIG. 5 illustrates a top cross-sectional view of a personal hygiene device according to yet another aspect of the present disclosure.
Figure 6:
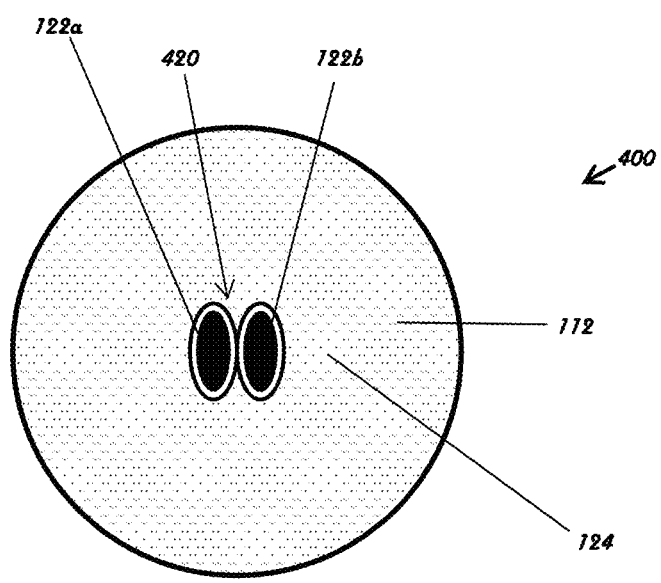
FIG. 6 illustrates a top cross-sectional view of a personal hygiene device according to yet another aspect of the present disclosure.

Various embodiments of sensors are described herein, and it will be understood that each of these embodiments may share certain similarities with other embodiments. In some aspects, the entire conductor is encapsulated within the insulating material 124. Referring to FIGS. 3-5, in some aspects, a dielectric gap 123 is defined by the space between the first conductor 122*a* and the second conductor 122*b*. As shown in the illustrative embodiment of FIGS. 3-4, the dielectric gap 123 of sensor 220 may have disposed within it a suitable dielectric material 130 (e.g., air, hydrogel, etc.). The dielectric material 130 may be disposed at least partially between the first conductor 122*a* and the second conductor 122*b* and may exhibit insulating properties.

Referring to FIGS. 3-6 in some aspects, the dielectric material 130 within the dielectric gap 123 may comprise one material or a plurality of suitable materials. In some aspects, the dielectric material 130 may include insulating material 124. In a further aspect, the dielectric material 130 is entirely comprised of insulating material 124. Alternatively, the dielectric material 130 may comprise a different composition and exclude the insulating material 124 entirely.

Referring to FIG. 4, the sensor 220 has a dielectric material 130 (e.g., in the dielectric gap 123 shown in FIG. 2) disposed between the first conductor 122*a* and the second conductor 122*b*. The dielectric material 130 may be a semi-permeable material such that liquid can pass through it. Dielectric material 130 may comprise a porous material that exhibits hydrophilic properties. In some aspects, the dielectric material 130 includes a hydrogel. The hydrogel may be composed of biocompatible materials having varying dielectric properties and relative permittivity. As shown in FIGS. 4-5, the dielectric material may be formed to have different shapes and dimensions. As shown in the embodiment of FIG. 4, the sensor 220 may have dielectric material 130 that generally complements the shape of the insulating material 124 (e.g., having a circular cross section). As shown in the embodiment of FIG. 5, a sensor 320 may include dielectric material 130 that partially surrounds or overlaps the insulating material 124.

For some aspects of a capacitive sensor, it may be advantageous to maintain the width of the dielectric gap 123 approximately constant. As such, it may be necessary for the dielectric material 130 to be rigid enough to support the structure of the sensor 220 and to withstand reasonably-expected compressive, tensile, and shear forces acting on the sensor during normal use.

The sensor 120, 220 may have an approximately circular cross section when looking in an axial direction extending from the proximal end 114 to the distal end 116 of the main body 110. In some aspects, the sensor 120, 220 may include a plurality of cross sections corresponding to a plurality of conductors. Referring to FIG. 2, a sensor having two conductors, a first conductor 122*a* and a second conductor 122*b*, may have two circular cross sections approximately adjacent one another, each of the two cross sections corresponding to the first and second conductors, respectively. In some aspects, as depicted in the illustrative embodiment of FIG. 6, a sensor 420 may have a non-circular oval cross section. In further aspects, the sensor may have a substantially rectangular cross section. It will be understood that the sensor cross section is not limiting, and the present disclosure encompasses other shapes that would result in a suitable sensor.

Referring now to FIGS. 9-12, a capacitive sensor 120 or 220 may generate an electric field 140. Properties of the electric field 140 and the capacitance of the sensor 120 are affected by numerous parameters, for example the surface area of conductors 122a and 122b, the distance between conductors 122a and 122b, and the material disposed within the dielectric gap 123. As such, when one or more factors affecting capacitance are changed, such a change may be detected and may be indicative of an environmental change such as a fluid within the electric field of the capacitive sensor 120 or 220.

In some aspects, it may be advantageous to maintain as short a distance as possible between conductors 122a and 122b to improve capacitance and sensor accuracy. Although the sensor is scalable, it will be understood that the personal hygiene product should not be sized such that it is unreasonably large or small for any of its intended uses. According to some aspects, the insulating material 124 may be a thin layer, such that the separation between the conductor 122 and the absorbent material 112 is minimal. Moreover, the amount or percentage of open (air or fixed dielectric) surface area between the conductors 122a and 122b (as opposed having a fluid disposed there between) may facilitate a detection of the dielectric constant change when a fluid enters the system. For example, k=1 for air, but k~50 for a fluid.

The capacitance of a parallel plate capacitor may be calculated with the following formula:

$$C = \frac{k\epsilon_0 A}{d},$$

where C is the capacitance, k is the relative permittivity of the material between the conductors, A is the area of the conductors, d is the distance between the conductors, and $\epsilon_0$ is a constant corresponding to the permittivity of free space in a vacuum ($8.8542 \times 10^{-12}$ F/m). A parallel plate model is presented herein to explain concepts, but one skilled in the art will appreciate that the capacitance of an actual system will be more accurately described with complex models.

In some aspects, the area of the conductors A and the distance d between conductors 122a and 122b (corresponding to the dielectric gap 123) may be kept substantially constant. The dielectric layer 130 disposed in the dielectric gap 123 between conductors 122a and 122b may be configured to have a variable composition such that its relative permittivity k changes. In some aspects, the dielectric material 130 has a first relative permittivity value when the dielectric material does not include a liquid and a second relative permittivity value when the dielectric material includes a liquid. The physical and chemical composition of the dielectric material having liquid may be different from that of the dielectric material lacking liquid, and so the first and second relative permittivity values may be different as well. According to some aspects, the dielectric material that includes liquid will have a higher relative permittivity k than the same dielectric material that does not include liquid. In such aspects, the capacitance C may be greater for dielectric material having liquid than for dielectric material lacking liquid.

In operation, if a liquid becomes disposed at least partially within the dielectric gap 123, the capacitance of the sensor 120 changes. This change may be detected by a circuit in communication with the sensor 120 (or the sensor 120) and communicated to an external device.

Figure 7:
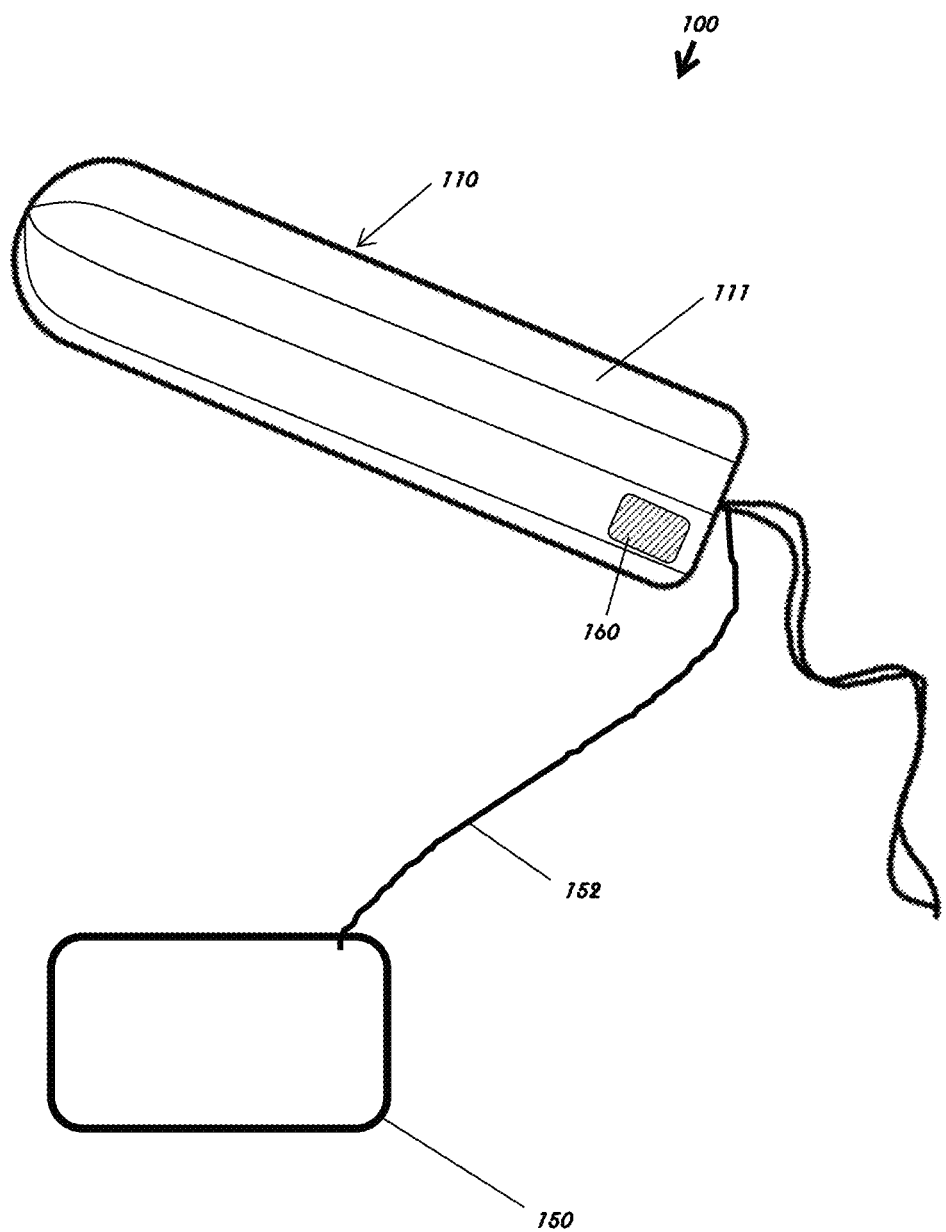
FIG. 7 illustrates a side perspective view of a personal hygiene device physically connected to a controller according to an aspect of the present disclosure.
Figure 8:
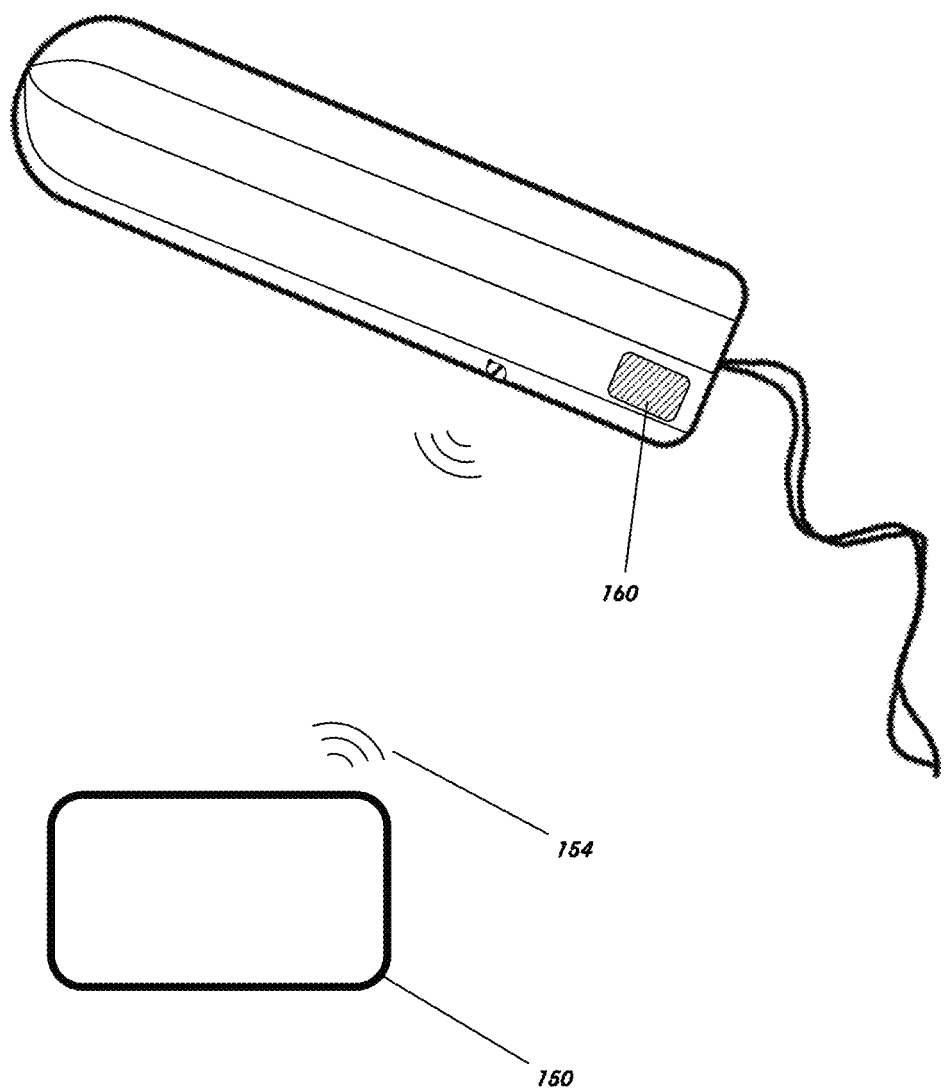
FIG. 8 illustrates a side perspective view of a personal hygiene device wirelessly connected to a controller according to another aspect of the present disclosure.
Figure 9:
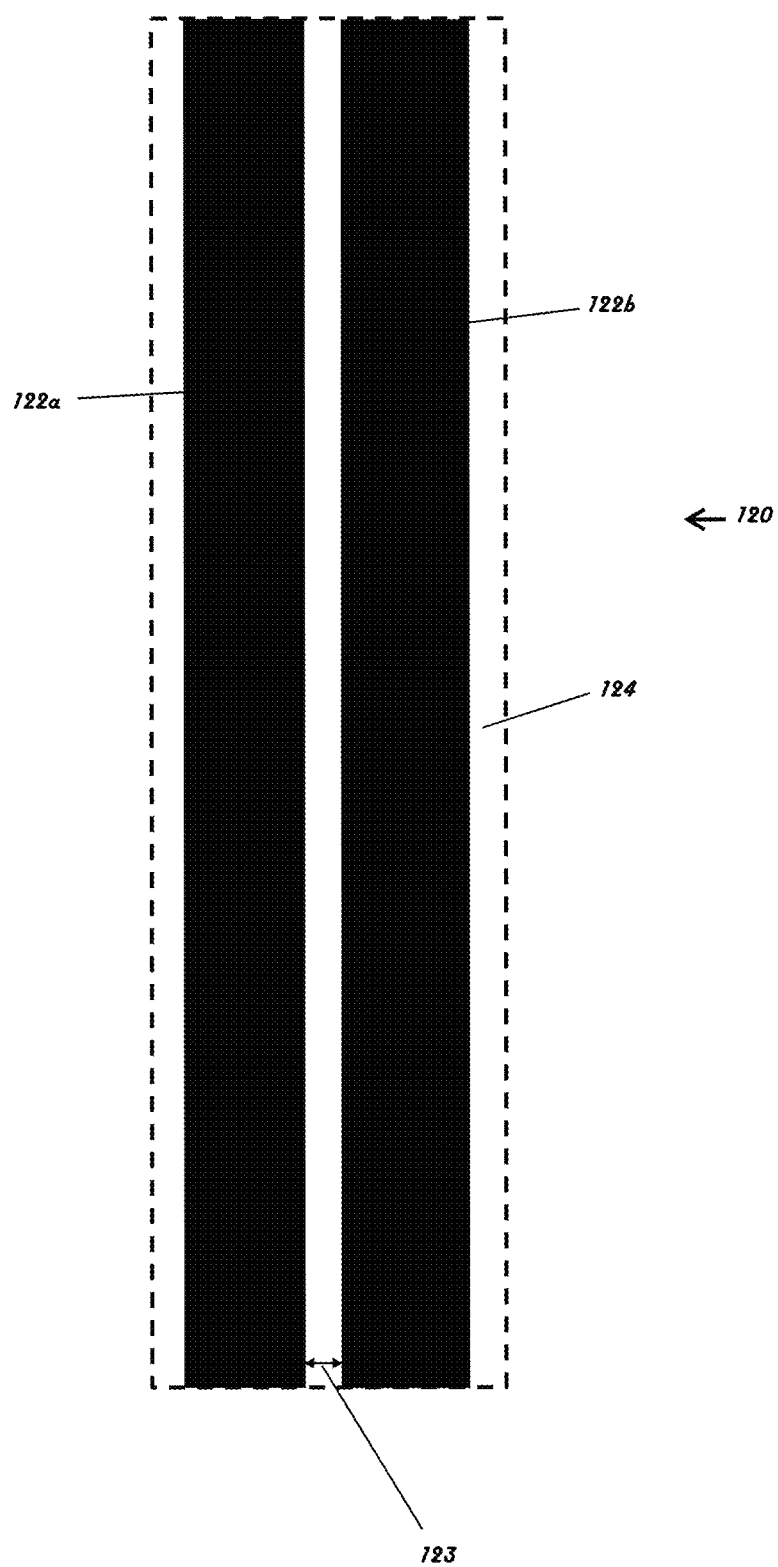
FIG. 9 illustrates a front planar view of a sensor according to an aspect of the present disclosure.
Figure 10:
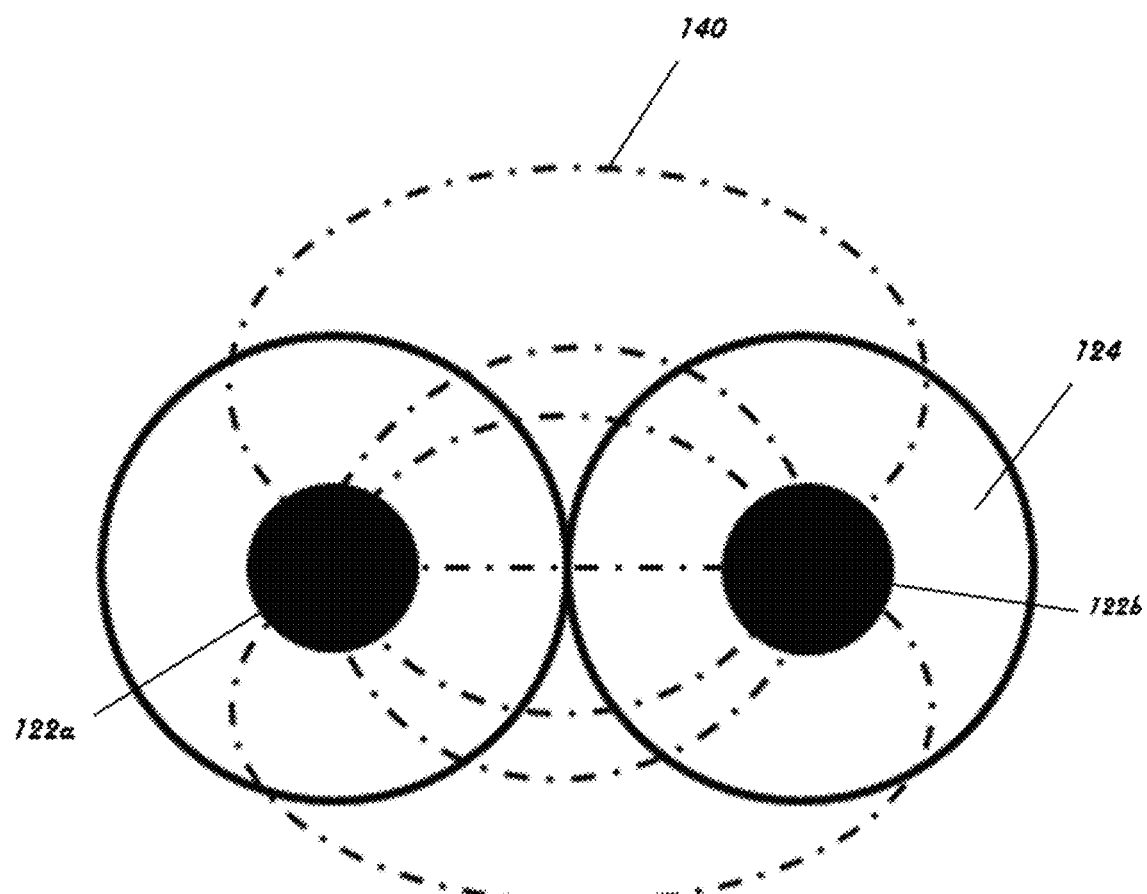
FIG. 10 illustrates a top planar view of the sensor illustrated in FIG. 9.
Figure 11:
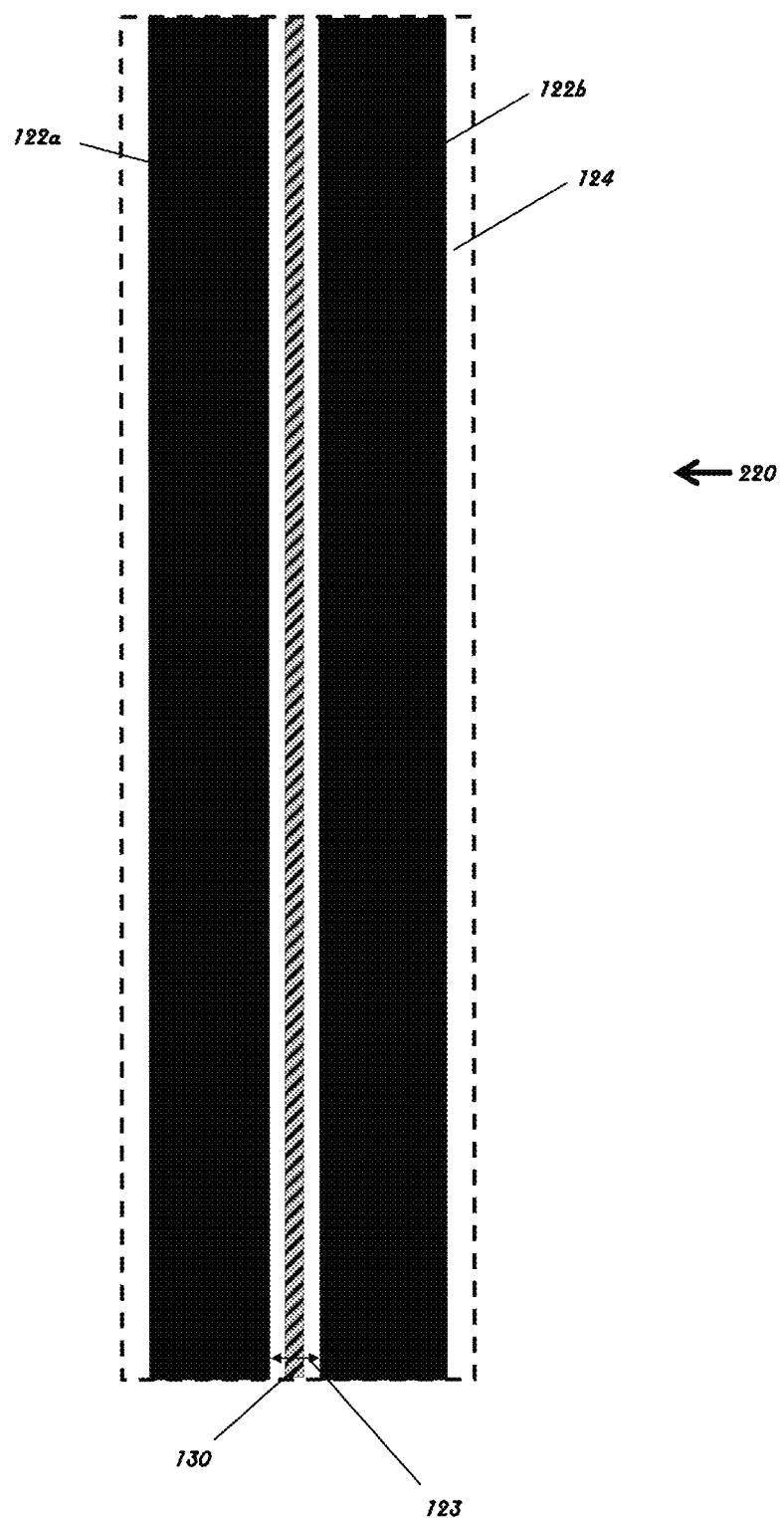
FIG. 11 illustrates a front planar view of a sensor according to another aspect of the present disclosure.
Figure 12:
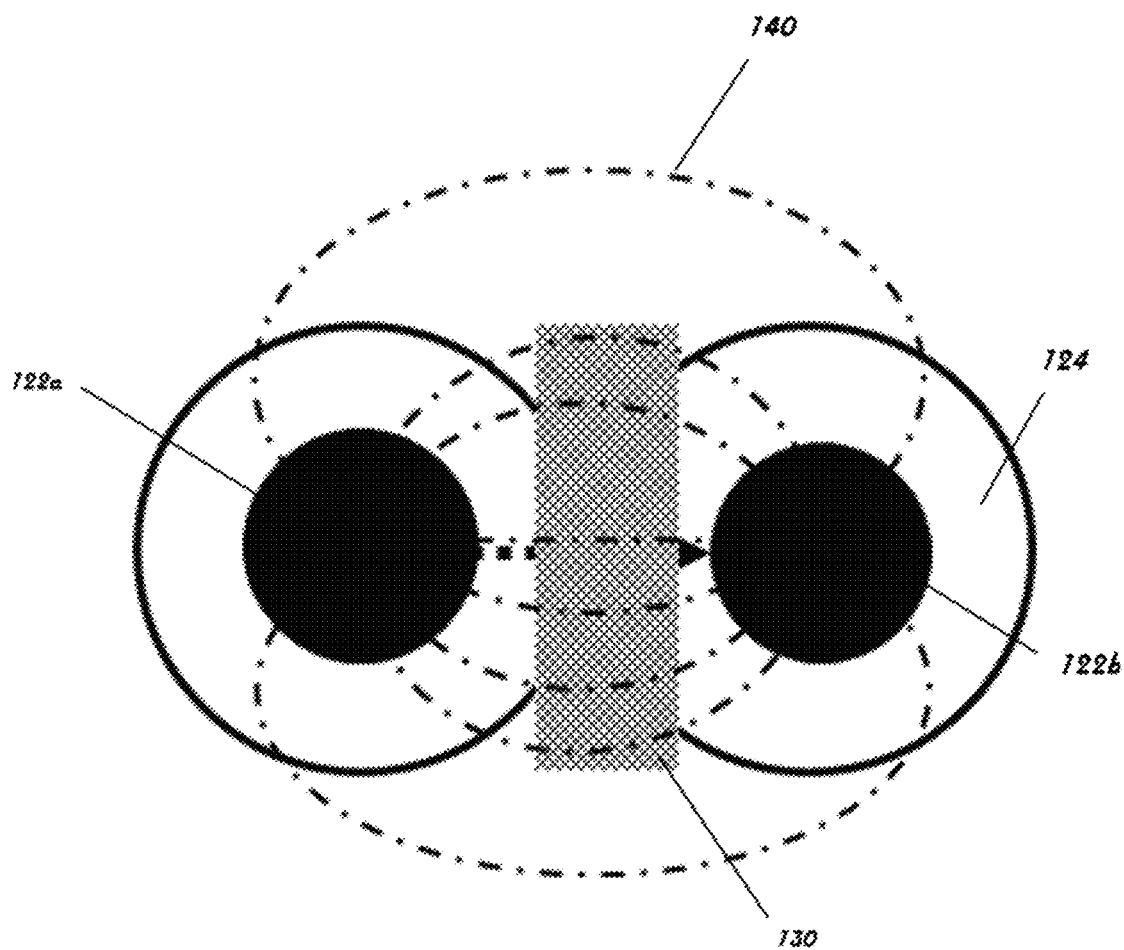
FIG. 12 illustrates a top planar view of the sensor illustrated in FIG. 11.

In some aspects, the personal hygiene device 100 may be connected to a controller 150. The controller 150 may receive data from the sensor 120. In some cases, the controller 150 may carry out a calculation or to further relay information to another device. Controller 150 may be a printed circuit board or a computing device, such as, but not limited to, a proprietary interface device, a cellular phone, a wrist watch, an electronic bracelet, or a personal computer. The controller 150 may be configured to provide a user with information corresponding to the sensor 120. Information may include, for example, detection of liquid within the sensor, the quantity of liquid detected, the consistency of the liquid, and the duration of presence of liquid within the personal hygiene device. Referring to FIGS. 7-8, the controller 150 may be connected through a physical wire 152 to the personal hygiene device 100. Alternatively, it may be connected through wireless communication 154. Wireless communication may include, but is not limited to, Wi-Fi, Bluetooth, ANT, radio frequency, infrared, near-field communication, or another suitable wireless interface. Controller 150 may be physically attached to the personal hygiene device 100, for example disposed on the main body 110 or within the absorbent material 112 of the main body 110. Alternatively, controller 150 may be separate from the main body 110.

The controller 150 may be in communication with a user device such as smart phones, personal computers, tablets, servers, cloud services, and the like. In some aspects, the sensor system such as sensor 120 is capable of wireless communication with a user device via the controller 150 or a transceiver. The user device may comprise a software application, which may comprise, for example, an interface that quantifies the user-based data received and generates a visual representation of quantified data for the user, including but not limited to, for example, generation of a chart, display, or alert for the user.

In some aspects, the software application may be able to provide the user with visual representation of the level of absorption by the personal hygiene product based on liquid absorption capacity and actual body fluid absorption. In some aspects, the software application may be able to provide the user with time frame for absorbency and anticipated saturation points. In some aspects, the software application may generate an alert signal to the user if saturation of the personal hygiene product is impending or reached. In some aspects, the software application may generate a visual representation of the quantified data, including but not limited to, for example, the user's rate of bodily fluid discharge or historical data of bodily fluid discharge.

In some aspects, the software application may be capable of accumulating data generated over time from use of multiple personal hygiene products. In some aspects, the software application may be able to generate a graphic, chart, or other interface to illustrate a baseline for the body fluid discharge based on the historical data. In some aspects, the software application may be able to generate predictive analytics and communicate that information to a user. Such information may allow the user to anticipate start and end dates, for example, if the personal hygiene product with a sensor system is used for a menstruation cycle. Such information may allow the user to understand the course of a cycle, including days or time periods of heavier or lighter flow.

In some aspects, a software application may generate information on a consumable usage rate for the user, predicting how many personal hygiene products are needed, including but not limited to, for example, per day, per week, or per cycle. In some aspects, a software application may generate a reminder or warning for a user to purchase personal hygiene products, including but not limited to, for example, when a start date for menstruation has been identified. In some aspects, a software application may provide the user an order quantity estimation based on historical data of the user's bodily fluid discharge. In some aspects, the interface of the software application may provide a direct link to an internet-based consumer service where a user may order and purchase additional personal hygiene products for direct delivery. In some aspects, the software application may be capable of automatic direct order placement based on consumable usage rate for delivery direct to user. The software application may facilitate purchase of additional personal hygiene products. The software application may connect the user to internet-based consumer services.

In some aspects, the personal hygiene device 100 may be configured to connect to a power source 160. The power source 160 may provide power to the sensor 120, the controller 150, a wired or wireless communication 152 or 154, or another element associated with the device. The power source 160 may be coupled to the main body 110. In some aspects, power source 160 may be a battery.

The sensor 120 may be configured to have an "on" state and an "off" state. In the "on" state, sensor 120 may receive a charge within its conductors 122 and actively communicate with the controller 150. In the "off" state, the conductors 122 are not charged, and data is not communicated to the controller 150. In some aspects, the sensor 120 may be configured to switch from the "off" state to the "on" state when it is removed from a protective wrapping, such as a shipping container or retail packaging. In another aspect, the sensor 120 may be manually switched from the "off" state to the "on" state by the user. The user may turn the sensor on via a physical switch or via a command within the controller 150. In a further aspect, sensor 120 may be switched to an "on" state automatically when an external condition is met, for example, when the personal hygiene device is in physical proximity to the controller 150.

The sensor 120 may be configured without binary "on" and "off" states. For example, the sensor 120 may have a continuum of states. The sensor 120 may be a passive component. The sensor 120 may generate signals and/or changes in states based on movement of the fluid around the sensor. The sensor 120 may comprise capacitor having a capacitance that fluctuates based on the fluid around the sensor 120. Changes (e.g., changes in capacitance) in sensor 120 may be measured by the controller 150. In some scenarios, the sensor 120 may be configured to perform measurements and/or signal conditioning before sending signals or fluctuations in signals to the controller 150. For example, the sensor 120 may be configured to filter out signals below a threshold change, noise, and/or the like.

Figure 13:
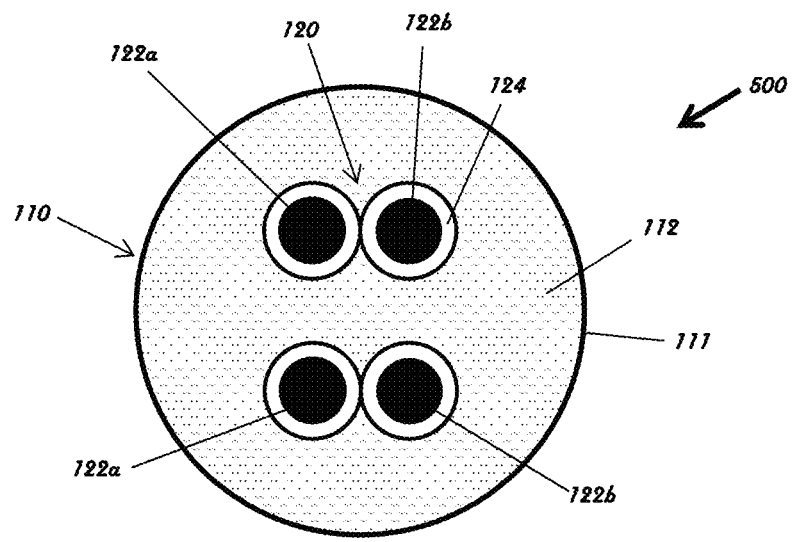
FIG. 13 illustrates a top cross-sectional view of a personal hygiene device according to another aspect of the present disclosure.

FIGS. 13-20 depict additional, non-limiting alternative aspects of this disclosure. FIG. 13 shows a personal hygiene device 500 having a plurality of sensors 120. As shown in the aspect of FIG. 13, sensors 120 may be disposed near the center of the main body 110 such that the conductors 122a, 122b extend in a first direction and then loop back in a second opposite direction, for example, to maximize conductive surface area. Although FIG. 13 illustrates a cross section of the device 500, it is understood that the conductors 122a, 122b are shown extending into and out of the page. In some aspects, the sensor 120 may be positioned close to the surface of the main body 110. As shown in the illustrative aspect of FIG. 14, a personal hygiene device 600 includes sensors 120a, 120b, 120c, and 120d that are positioned radially around the centerline of main body 110. As described in reference to FIG. 13, the sensors 120a-d, may comprise a pair of conductors 122a, 122b that are looped to extend into and out of the page, but are formed form a continuous thread or wire. Alternatively, the conductors 120a-d may comprise distinct conductors, each configured to sense a portion of the device 500.

Figure 15:
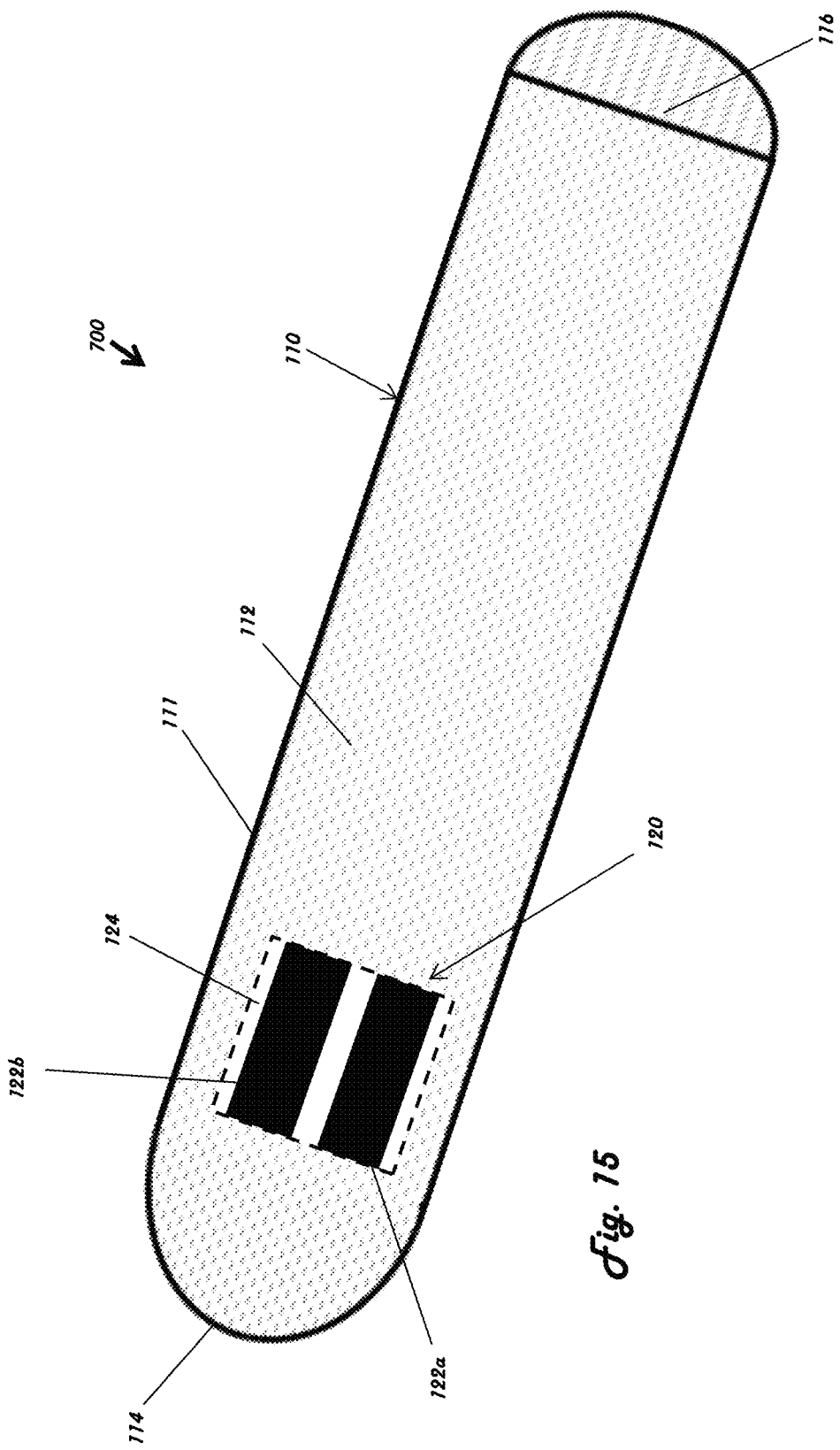
FIG. 15 illustrates a side cross-sectional view of a personal hygiene device according to yet another aspect of the present disclosure.
Figure 16:
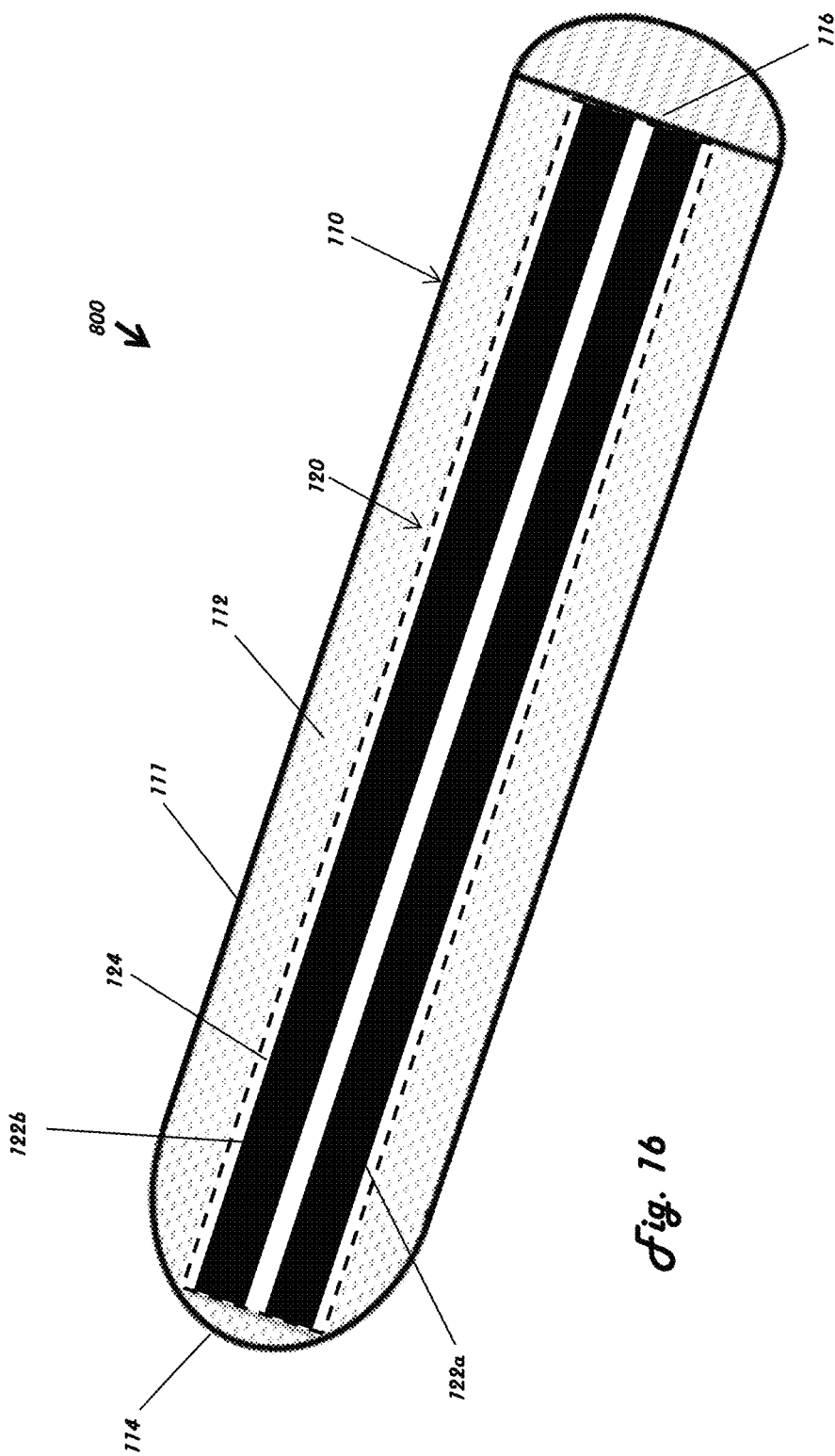
FIG. 16 illustrates a side cross-sectional view of a personal hygiene device according to yet another aspect of the present disclosure.

FIGS. 15-17 depict aspects having various sensor configurations within the main body 110. In some aspects, as illustrated in FIG. 15, a personal hygiene device 700 may have a sensor 120 that is positioned within the main body 110 such that the sensor 120 is closer to the proximal end 114 than to the distal end 116. Alternatively, the opposite aspect is also possible where the sensor 120 is closer to the distal end 116 than to the proximal end 114. FIG. 16 depicts a personal hygiene device 800 that includes one sensor 120 that extends from proximal end 114 to distal end 116 substantially through the entire length of the main body 110. Additionally, the sensor 120 of device 800 may loop back and extend from the distal end 116 toward the proximal end 114 in a "U-shaped" configuration.

Referring to FIG. 17, a personal hygiene device 900 may include multiple sensors 120 disposed within the personal hygiene device 100. Although each consecutive sensor depicted in FIG. 17 is illustrated as separate from the preceding sensor by an approximately equal distance, it will be understood that the distance between individual sensors may vary.

Figure 18:
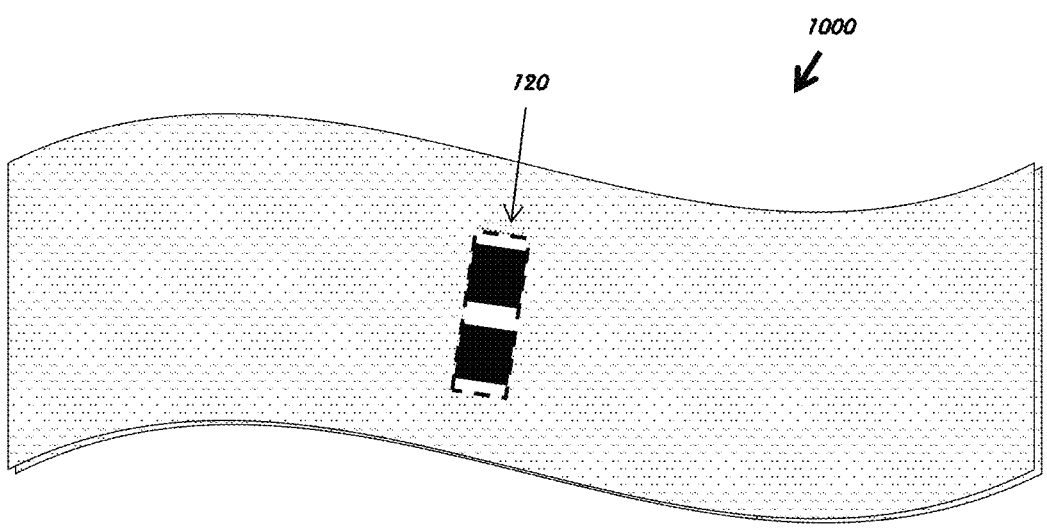
FIG. 18 illustrates an isometric view of a personal hygiene device according to yet another aspect of the present disclosure.

FIG. 18 depicts an aspect of the present disclosure in which the personal hygiene device is a sanitary napkin 1000. The sanitary napkin 1000 may comprise one or more layers. The one or more layers may comprise an absorbent material, such as absorbent fibers. The sensor 120 may be disposed within and/or between the one or more layers. The sensor 120 may be located in only a portion of the sanitary napkin 1000. In other implementations, the sensor 120 may extend along a length and/or width of the sanitary napkin 100. The one or more layers of the sanitary napkin may be surface treated as described further herein.

Figure 19:
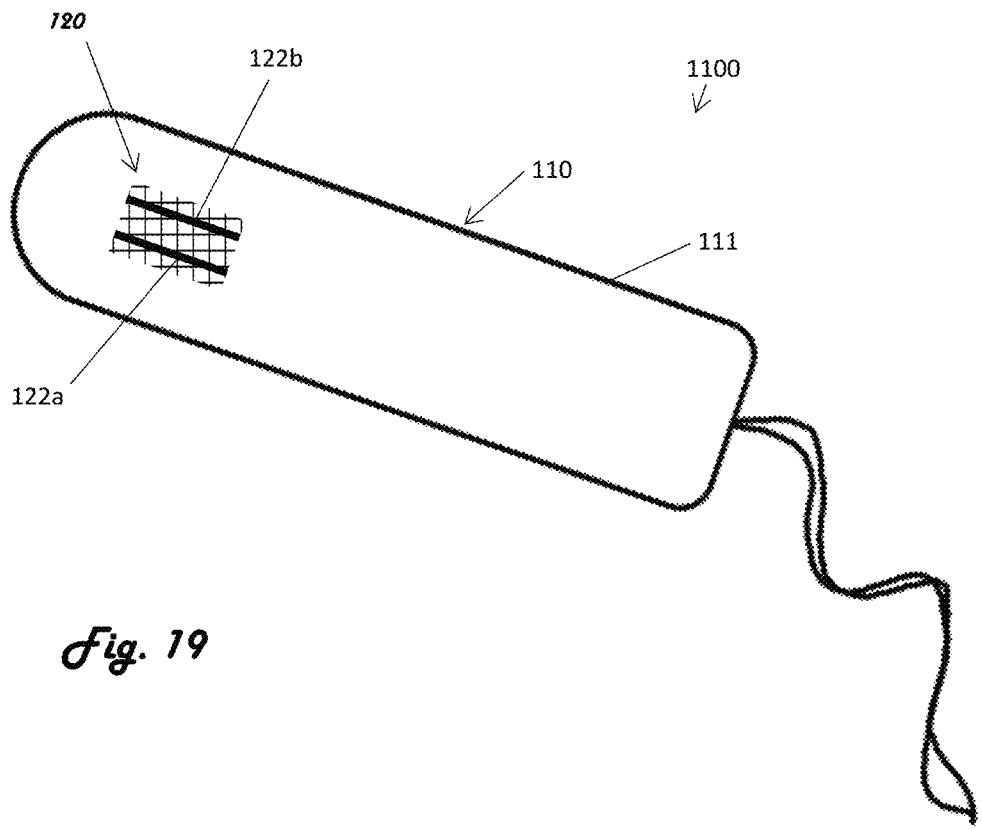
FIG. 19 illustrates a top cross-sectional view of a personal hygiene device according to yet another aspect of the present disclosure.
Figure 20:
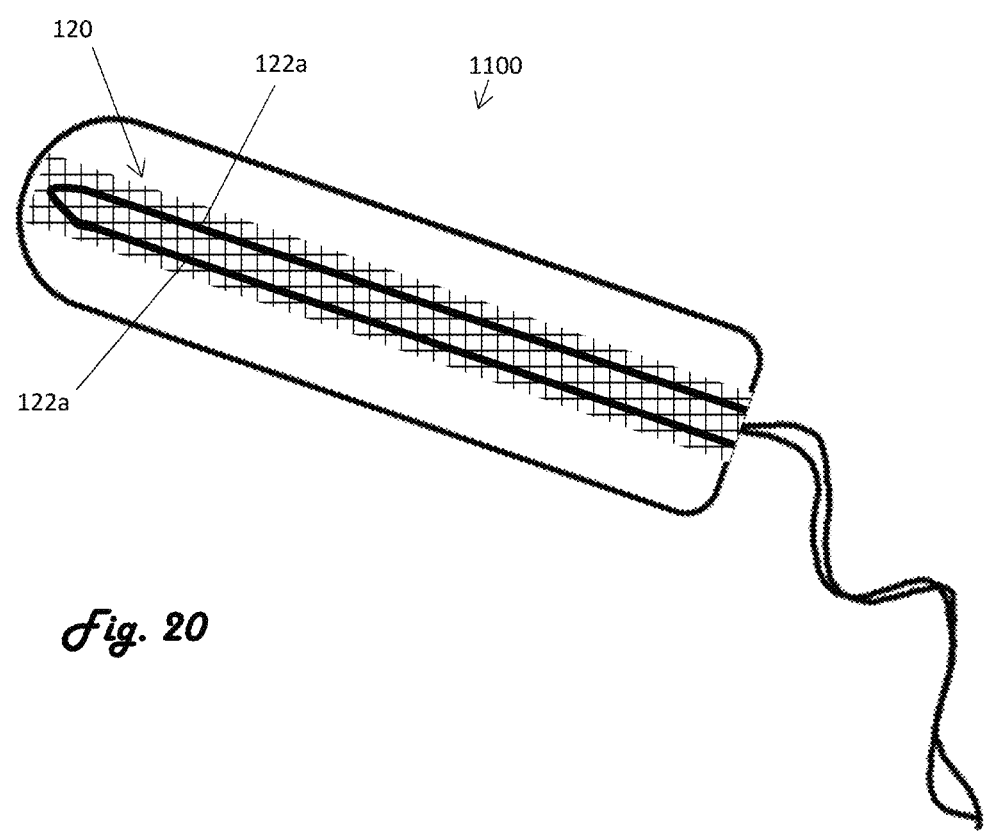
FIG. 20 illustrates a side cross-sectional view of the personal hygiene device of FIG. 19.

In some aspects, as illustrated in FIG. 19, a personal hygiene device 1100 may have a sensor 120 that is disposed within the main body 110. The sensor 120 may comprise generally parallel conductors 122a, 122b such as wires or conductive threads comprising a non-conductive core and conductive coating. The configuration of the conductors 122a, 122b may be operative as a capacitor extending along a length of the device 1100. FIG. 20 depicts the personal hygiene device 1100 showing the sensor 120 (e.g., conductors 122a, 122b) of device 1100 looping back in the insertion domed end of the personal hygiene device in a "U-shaped" configuration.

Aspects of the personal hygiene device as described herein offer a number of advantages over existing products. Some aspects provide active monitoring of absorption capacity of the personal hygiene product while a user is wearing or using it. The device may collect data about menstruation patterns, as well as other biometrics. Collected data may be used to instruct the user to adjust or replace the hygiene device so as to avoid oversaturation of the absorbent material and prevent unexpected outflow. This may help decrease the risk of associated health problems, such as infections, as well as to avoid unpleasant social interactions or embarrassment. Some aspects allow for collection of multiple variables, which can be used to predict likely health scenarios, as well as to provide data to a physician if necessary. Continuous monitoring may also be helpful in reminding a user to employ a new hygiene device even if the user forgets to do so, and the collected data may be used to alert the user in case of disruptions to normal or expected cycle patterns.

The term "plurality," as used herein, means more than one. The singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

The transitional terms "comprising," "consisting essentially of," and "consisting" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristics" of the claimed invention. Aspects described in terms of the phrase "comprising" (or its equivalents), also provide, as aspects, those which are independently described in terms of "consisting of" and "consisting essentially of."

When values are expressed as approximations by use of the antecedent "about," it will be understood that the particular value forms another aspect. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

When a list is presented, unless stated otherwise, it is to be understood that each individual element of that list, and every combination of that list, is a separate aspect. For example, a list of aspects presented as "A, B, or C" is to be interpreted as including the aspects, "A," "B," "C," "A or B," "A or C," "B or C," or "A, B, or C."

The terms "substantially parallel" as used herein in reference to two elements with respect to each other includes the two elements being close to, but not exactly, parallel to each other and the two elements being exactly parallel to each other. The terms "substantially perpendicular" as used herein in reference to two elements with respect to each other includes the two elements being close to, but not exactly perpendicular to each other, and the two elements being exactly perpendicular to each other.

Throughout this specification, words are to be afforded their normal meaning as would be understood by those skilled in the relevant art. However, so as to avoid misunderstanding, the meanings of certain terms will be specifically defined or clarified.

While the disclosure has been described in connection with the various aspects of the various figures, it will be appreciated by those skilled in the art that changes could be made to the aspects described above without departing from the broad inventive concept thereof. It is understood, therefore, that this disclosure is not limited to the particular aspects disclosed, and it is intended to cover modifications within the spirit and scope of the present disclosure as defined by the claims.

Features of the disclosure that are described above in the context of separate aspects may be provided in combination in a single aspect. Conversely, various features of the disclosure that are described in the context of a single aspect may also be provided separately or in any sub-combination. Finally, while an aspect may be described as part of a series of steps or part of a more general structure, each of the steps may also be considered an independent aspect in itself, combinable with others.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed:

1. A personal hygiene device comprising:
a personal hygiene product having an axial length comprising an absorbent core having a domed insertion end in a form suitable for insertion into a user's body to absorb menstrual fluid;
a capacitive sensor assembly disposed within the absorbent core, wherein the capacitive sensor assembly comprises at least a pair of linear conductive leads spaced from each other by a dielectric gap having disposed therein a dielectric material, the linear conductive leads configured to generate an electric field between each other when electric current is applied to one or more of the linear conductive leads, wherein the sensor further comprises an insulator disposed between the absorbent core and at least a portion of each of the conductive leads, wherein each pair of linear conductive leads form a single continuous thread of conductive material, the single continuous thread of conductive material having a u-shaped curvature in the domed insertion end;
a controller comprising a communication circuit capable of wireless communication with a user device; and
a signal transmission conduit extending from the capacitive sensor assembly and interconnecting the capacitive sensor assembly with the controller to facilitate transmission of information measured via the capacitive sensor assembly to the user device.

2. The personal hygiene device of claim 1, wherein the communication circuit is capable of low-power Bluetooth wireless communication with the user device.

3. The personal hygiene device of claim 1, wherein the communication circuit is capable of near-field wireless communication with the user device.

4. The personal hygiene device of claim 1, wherein the user device comprises a hand-held personal electronic device capable of interface with a user.

5. The personal hygiene device of claim 1, wherein the user device comprises a receiver and a software application capable of signaling or alerting a user based on data received from the capacitive sensor assembly.

6. The personal hygiene device of claim 1, wherein the user device comprises a software application capable of direct order and purchase of additional personal hygiene products through an internet-based consumer services.

7. The personal hygiene device of claim 1, wherein the user device comprises a software application capable of estimating order quantity based on historical data of bodily fluid discharge.

8. The personal hygiene device of claim 1, wherein the user device comprises a software application capable of predicting time and rate of bodily fluid discharge.

9. The personal hygiene device of claim 1, wherein the signal transmission conduit comprises a cable.

10. The personal hygiene device of claim 1, wherein the signal transmission conduit comprises conductive ink deposited on a flexible substrate.

11. The personal hygiene device of claim 1, wherein the insulator is treated to cause a surface of the insulator to be one or more of hydrophilic, hydrophobic, omniphilic, omnophobic, oleophilic, or oleophobic.

\* \* \* \* \*